United States Patent
Bartley et al.

(10) Patent No.: US 6,534,441 B1
(45) Date of Patent: Mar. 18, 2003

(54) NICKEL-RHENIUM CATALYST FOR USE IN REDUCTIVE AMINATION PROCESSES

(75) Inventors: William J Bartley, Charleston, WV (US); Ronald Gary Cook, Hurricane, WV (US); Kendrick Edward Curry, Hurricane, WV (US); Stefan Kent Mierau, South Charleston, WV (US)

(73) Assignee: Union Carbide Chemicals & Plastics Technology Corporation, Danbury, CT (US)

( * ) Notice: Subject to any disclaimer, the term of this patent is extended or adjusted under 35 U.S.C. 154(b) by 0 days.

(21) Appl. No.: 09/519,724

(22) Filed: Mar. 3, 2000

Related U.S. Application Data

(60) Provisional application No. 60/123,157, filed on Mar. 6, 1999.

(51) Int. Cl.$^7$ .............. B01J 21/08; B01J 21/12; B01J 21/14; B01J 23/00; B01J 23/08

(52) U.S. Cl. .............. 502/337; 502/241; 502/259; 502/263; 502/335; 502/355; 502/407; 502/415; 502/439

(58) Field of Search .............. 502/325, 326, 502/327, 328, 330, 332, 337, 338, 339, 340, 344, 349, 353, 355, 407, 414, 415, 439, 241, 259, 263, 335

(56) References Cited

U.S. PATENT DOCUMENTS

| | | | |
|---|---|---|---|
| 3,492,314 A | 1/1970 | Asano et al. | 260/343.6 |
| 4,111,840 A | 9/1978 | Best | 252/432 |
| 4,123,462 A | 10/1978 | Best | 260/585 |
| 4,255,357 A | 3/1981 | Gardner et al. | 564/480 |
| 4,625,030 A | 11/1986 | Best | 544/358 |
| 4,657,880 A * | 4/1987 | Lachman et al. | 502/64 |
| 4,665,195 A | 5/1987 | Stogryn et al. | 548/523 |
| 4,701,434 A | 10/1987 | Koll | 502/230 |
| 4,708,945 A * | 11/1987 | Murrell et al. | 502/263 |
| 4,795,733 A | 1/1989 | De Thomas | 502/327 |
| 4,855,505 A | 8/1989 | Koll | 564/398 |
| 4,863,890 A | 9/1989 | Koll | 502/230 |
| 4,912,260 A | 3/1990 | Dobson et al. | 564/480 |
| 4,918,234 A | 4/1990 | Deebs | 564/480 |
| 4,992,587 A | 2/1991 | Koll | 564/398 |
| 5,196,588 A * | 3/1993 | Burgess et al. | 564/480 |
| 5,202,491 A | 4/1993 | Burgess et al. | 564/480 |
| 5,321,160 A | 6/1994 | Hironaka et al. | 564/480 |
| 5,600,000 A | 2/1997 | King | 564/480 |
| 5,608,113 A | 3/1997 | Becker et al. | 564/480 |
| 5,750,790 A * | 5/1998 | King | 564/469 |
| 5,789,490 A * | 8/1998 | Chang | 525/403 |
| 5,817,593 A * | 10/1998 | Chang et al. | 502/207 |
| 5,891,820 A * | 4/1999 | King | 502/313 |
| 5,952,529 A * | 9/1999 | Chang et al. | 564/480 |
| 6,117,814 A * | 9/2000 | Piecha et al. | 502/325 |

FOREIGN PATENT DOCUMENTS

| | | |
|---|---|---|
| EP | 0737669 | 10/1996 |
| GB | 1319191 | 6/1973 |
| WO | 9638226 | 12/1996 |

OTHER PUBLICATIONS

International Search Report dated Sep. 11, 2001 issued by the EPO acting as the International Searching Authority in PCT/US01/40221.
Abstract: JP05168934–A –Jul. 2, 1993 –Japan.
Abstract: JP07323226–A –Dec. 12, 1995 –Japan.

* cited by examiner

*Primary Examiner*—Stanley S. Silverman
*Assistant Examiner*—Cam N. Nguyen

(57) ABSTRACT

A nickel/rhenium catalyst composition for the reductive amination of lower aliphatic alkane derivatives is described. The catalyst includes from about 2 to about 75 weight percent nickel and has a nickel to rhenium weight percent ratio of from about 1:1 to about 200:1. The nickel and rhenium are supported on an alumina-silica support which contains from about 5 to about 65 weight percent silica and has a BET surface area of from about 30 to about 450 m$^2$/g. A process for the reductive amination of lower aliphatic alkane derivatives using such a catalyst composition is also provided.

17 Claims, No Drawings

NICKEL-RHENIUM CATALYST FOR USE IN REDUCTIVE AMINATION PROCESSES

This Application claims the benefit of No. 60/123,157 filed Mar. 6, 1999.

The present invention relates to a catalyst for the reductive amination of lower aliphatic alkane derivatives. The catalyst comprises rhenium, nickel and, optionally, boron, supported on an alumina-silica support, wherein the alumina-silica support contains from about 5 to about 65 weight percent silica and has a BET surface area of from about 30 to about 450 $m^2/g$. The catalyst provided by the invention has increased activity as well as selectivity to a specified mix of polyamine products.

BACKGROUND OF THE INVENTION

The reductive amination of lower aliphatic alkane derivatives, i.e., diols such as ethylene glycol and alkanolamines such as monoethanolamine, is a commercially important family of processes. A variety of catalyst compositions for this purpose are found in the literature and are used commercially. Many are based on nickel/rhenium mixtures deposited on a support material. For example, U.S. Pat. No. 4,795,733 to DeThomas relates to nickel/rhenium catalyst compositions also containing a Group VIII metal having an atomic number greater than 43. The catalyst composition is supported on a material such as carbon, magnesium silicate, bentonite, zeolite, metal alloys, silica-alumina, and magnesium oxide-silicon oxide mixtures. Preferred as a support material is gamma-alumina.

PCT Application No. WO 96/38226 discloses catalyst compositions comprising rhenium, nickel, cobalt, boron and copper and/or ruthenium deposited on a support material. Disclosed support materials are silica, aluminum, and/or titanium, preferably silica or alumina, particularly alpha-alumina, silica, silica-alumina, kieselguhrs, diatomaceous earths, or silica-titania, most preferably silica. Surface areas of 10 to 500 $m^2/g$, more preferably from 40 to 200, $m^2/g$ are disclosed.

U.S. Pat. No. 5,202,491 to Burgess et al. discloses a continuously generated alkyleneamines composition that may be produced using a variety of nickel-containing catalyst compositions. The patent also discloses that the catalysts may be supported using a number of support materials, including silica-alumina.

Finally, U.S. Pat. Nos. 4,111,840 and 4,123,462 to Best disclose catalyst compositions comprising nickel and rhenium impregnated on a support material selected from alpha-aluminas, silica, silica-alumina, kieselguhrs, diatomaceous earths, and silica-titania, wherein the mole ratio of nickel to rhenium ranges from about 2:1 to about 30:1 and the catalyst is activated by reduction in the presence of hydrogen at elevated temperature.

The Best patents teach that not all support materials are equivalent and that higher surface area supports lead to more active Ni/Re catalyst compositions. However, the data provided in these patents do not support this conclusion. In particular, the data provided in Example 4 of the Best patents show that neither support surface area nor metal loading provides a statistically significant effect on catalyst activity, while the data provided in Example 5 in both references show that increasing the surface area of the support reduces the activity of the catalyst.

It is not clear why a rate effect is seen with respect to Example 5 and no such effect is shown in Example 4, particularly since the catalyst compositions and the reaction conditions are so similar. These inconsistent teachings lead to the conclusion that, at best, increasing the surface area of the support reduces the activity of the catalyst only under some circumstances.

Table 1 of the '840 patent discloses several examples of commercially available, useful support materials, including the following containing both silica and alumina:

| Support | Surface Area ($m^2/g$) | Percent Silica |
| --- | --- | --- |
| Girdler T869 | ~60 | 95.1 |
| Girdler T1571 | ~150 | 93 |
| Girdler T372 | ~40 | 0.2 |
| Girdler T373 | 2–3 | 0.2 |
| Girdler K306 | ~250 | 88 |
| Girdler T2085 | ~113 | 97.4 |
| Girdler K10 | ~268 | 81 |
| Grace 980–13 | ~375 | 87 |
| Grace 980–25 | ~375 | 75 |

Reductive amination produces a variety of products, some of which have greater economic value than others, depending on current market requirements. For example, the reductive amination of monoethanolamine (MEA) produces lower molecular weight linear polyamine products, such as ethylenediamine (EDA), aminoethylethanolamine (AEEA), and diethylenetriamine (DETA). EDA is a highly commercially valuable product at present, and market demand also exists for AEEA and DETA. Higher molecular weight linear polyamines, such as diamine and triamine, and/or cyclic polyamine products, such as piperazine (PIP), hydroxyethylpiperazine (HEP), aminoethylpyrazine (AEP) and heavy polyamine oligomers, are also formed. Although these products tend to be less valuable than the lower molecular weight polyamine products, there is often an economic incentive for their production. Accordingly, for maximum economic benefit the catalyst compositions used in commercial reductive amination processes must be selective to the desired mixture of polyamine products, in addition to being highly active.

The prior art has not appreciated how to control catalyst composition and preparation variables in a manner that provides a catalyst which has a specified activity and which is selective for a particular mix of products. For example, a statistical analysis of the data presented in Example 4 of the Best '840 patent leads to the conclusion that support surface area has no statistically significant effect on the EDA/PIP ratio. This is also the case with the data presented in Example 5 of the Best '462 patent. In fact, if any effect is shown in this data, it is that increasing the surface area of the support decreases the EDA/PIP ratio. Examples I and F of U.S. Pat. No. 5,600,000 suggest that under some circumstances and in the presence of certain promoters, metal loading can have an effect on catalyst activity; however, the effects of surface area and other important catalyst preparation variables were not considered.

It has now been discovered that nickel/rhenium catalyst compositions supported on alumina-silica containing from about 5 to about 65 weight percent silica and having a BET surface area of from about 30 to about 450 $m^2/g$ (as measured by the method of Brunauer, Emmitt and Teller) are especially advantageous for the production of polyamine products. By appropriately selecting the composition of these catalysts and controlling certain catalyst preparation variables, it is possible to provide catalysts which have a desired activity and which are capable of providing a specified mix of polyamine products.

Accordingly, the catalysts taught by the invention can be used to provide a mix of polyamine products characterized by very favorable ratios of lower molecular weight polyamines, such as EDA, AEEA and DETA, to less favorable higher molecular weight linear and cyclic products such as diamine, triamine, PIP, and HEP. However, should market demands change, the catalyst composition can be appropriately adjusted and the conditions for preparing the catalyst controlled in a manner such that the catalyst is relatively more selective for the higher molecular weight linear and cyclic polyamine products.

SUMMARY OF THE INVENTION

The present invention provides a catalyst composition for the reductive amination of a lower aliphatic alkane derivative. The catalyst composition comprises nickel and rhenium as active metals. More particularly, the catalyst comprises from about 2 to about 75 weight percent nickel and has a nickel to rhenium weight percent ratio of from about 1:1 to about 200:1. The catalyst is supported on an alumina-silica support which contains from about 5 to about 65 weight percent silica and has a BET surface area of from about 30 to about 450m$^2$/g. The catalyst optionally comprises boron and has a boron to nickel weight percent ratio less than or equal to about 1. The nickel content of the catalyst, the nickel to rhenium and boron to nickel weight percent ratios, the support surface area, and the silica content of the support are selected to provide the catalyst composition with a specified activity, and to provide a particular mix of polyamine products when the lower aliphatic alkane derivative is reductively aminated in the presence of the catalyst composition.

In a second aspect, the invention provides a process for the reductive amination of a lower aliphatic alkane derivative to produce a specified mix of polyamine products. The process comprises contacting the lower aliphatic alkane derivative with ammonia or an amine under reducing conditions in the presence of the catalyst composition described above to produce a particular mix of products.

DETAILED DESCRIPTION OF THE INVENTION

As noted above, the catalyst composition contains nickel and rhenium as the active metals. In general, the amount of nickel in the catalyst composition is from about 2 to about 75 weight percent, based on the total weight of the composition. Depending on the lower aliphatic alkane derivative being aminated, the amount of nickel may vary. For the reductive amination of diols, for example, ethylene glycol and propylene glycol, the preferred amount of nickel in the catalyst composition is generally higher and ranges from about 10 to about 75 weight percent, more preferably from about 10 to about 50 weight percent. For the reductive amination of other lower aliphatic alkane derivatives such as monoethanolamine or ethylenediamine, the preferred amount of nickel in the catalyst composition varies from about 2 to about 30 weight percent, more preferably from about 5 to about 15 weight percent, based on the total weight of the composition.

The weight percent ratio of nickel to rhenium in the catalyst composition is preferably in the range of from about 1:1 to about 200:1, more preferably from about 1:1 to about 100:1, most preferably from about 2:1 to about 50:1.

The catalyst may optionally comprise boron as well. In those embodiments where boron is added to the composition, boron to nickel weight percent ratios are selected to range up to about 1, and preferably up to about 0.5. It is known in the art to use boron as a promoter to obtain high EDA selectivities in nickel/rhenium catalyst compositions. However, the use of boron has disadvantages, such as the suppression of catalytic activity, more complicated and expensive catalyst preparation and contamination of the polyamine products by leached boron. It is therefore preferable to use little or no boron in the catalyst compositions of the invention. Unexpectedly, good activities and selectivities to linear polyamine products can be achieved without adding boron to the catalyst composition by appropriate adjustment of the remaining catalyst variables.

The catalyst composition is supported on an alumina-silica support containing from about 5 to about 65 weight percent silica. The remainder of the support is alumina. The BET surface area of the alumina-silica ranges from about 30 to about 450 m$^2$/g. The use of alumina-silica having these properties is critical to achieving the high activities and selectivities of the present invention. The alumina-silica preferably contains from about 10 to about 50 weight percent silica. A particularly preferred catalyst composition is made with a support material containing about 20 weight percent silica and about 80 weight percent alumina. In the most preferred embodiment of the invention, the alumina phase of the alumina-silica support material substantially comprises theta-alumina and the silica phase is largely amorphous. Preferably, the BET surface area of the alumina-silica is from about 35 to about 300 m$^2$/g, more preferably from about 50 to about 200 m$^2$/g. It has been found that where enhanced EDA production is desired, the preferred surface area of the alumina-silica varies somewhat depending on whether or not the catalyst composition comprises boron. The preferred BET surface area is typically higher in boron-free catalyst compositions. For instance, the most preferred BET surface areas for boron-containing catalyst compositions range from about 60 to about 150 m$^2$/g, while the most preferred BET surface areas for boron-free catalyst compositions vary from about 100 to about 400 m$^2$/g.

The pore volume of the alumina-silica may be varied within a wide range, so long as the surface area requirements are met. Generally, the pore volume of the alumina-silica may range from about 0.2 to 1.5 cc/g, preferably from about 0.5 to 1.0 cc/g.

Alumina-silicas having an appropriate combination of the above properties are not generally commercially available. However, preparation of such materials is well within the abilities of one skilled in the art of support material manufacture. The support material may be provided in any form commonly employed in the art, including tablets, extrudates, spheres, powders, and other forms well-known to those skilled in the art.

The particular method of incorporating the alumina-silica supports with nickel and rhenium is not critical; however, impregnated catalyst compositions generally perform better than precipitated catalyst compositions, unless very high metal loadings are being used. The amount of metals provided on the alumina-silica support can affect or vary the catalytic activity or selectivity.

One technique for impregnating the nickel and rhenium onto the support is by an incipient wetness techniques using aqueous solutions of salts of the metals. Various organic and inorganic salts may be used in the impregnation solutions. Examples of suitable nickel-containing salts for impregnation are nickel nitrate hexahydrate, nickel formate, nickel acetate tetrahydrate, nickel acetate, nickel chloride, nickel carbonate and the like. Typical rhenium salts employed include ammonium perrhenate, perrhenic acid, rhenium heptoxide and other salts typically used by those skilled in the art. Boron compounds include orthoboric acid, ammonium hydrogen tetraborate, ammonium tetraborate and other compounds known in the art.

In preparing the impregnation solutions, the total amount of metal desired to be impregnated on a specific quantity of support and the relative weight ratio of nickel to rhenium should be considered. Both factors have been found to affect the final properties of the catalyst compositions. As noted above, for the reductive amination of lower aliphatic alkane derivatives such as monoethanolamine or ethylenediamine, the total nickel content is preferably in the range of from about 2 to about 30 weight percent based on the total weight of the catalyst composition, more preferably from about 5 to about 15 weight percent. For the reductive amination of diols such as ethylene glycol, the total nickel content is preferably in the range of from about 10 to about 50 weight percent, more preferably from about 10 to about 25 weight percent. As also noted above, the weight percent ratio of nickel to rhenium in the catalyst composition is preferably in the range of from about 1:1 to about 200:1, more preferably about 1:1 to about 100:1, and most preferably from about 2:1 to about 50:1.

It may also be advantageous to pre-dry the alumina-silica support prior to impregnation in order to ensure that the support will take up as much of the solution as possible. Pre-drying also enables the metal to permeate more deeply into the support during impregnation. Penetration of the metal into the support may be further increased by techniques known to those skilled in the art such as increasing the time the support is in contact with the solution. Other impregnation techniques are well known in the art and may be utilized.

Where relatively large amounts of metal are to be impregnated on the support, a single impregnation step may not be sufficient. Although an impregnation solution may be prepared with the minimum amount of solvent required to dissolve the metal salts, the total amount of the impregnation solution may be greater than that which the support can absorb. In such cases, a portion of the impregnation solution approximately equal to the absorption volume of the support is initially contacted with the support. After contacting, the support is dried and then contacted with an additional amount of impregnation solution. Drying may be accomplished by any technique which sufficiently evaporates the volatile constituents of the impregnation solution. The sequential steps of contacting the support with the solution and then drying are continued until all of the impregnation solution is used. A typical drying step can comprise heating the impregnated support at an elevated temperature, e.g., 100–120° C. for several hours. Evacuation drying may also be used where the support is cooled and reduced under pressure. Additionally, drying may by accomplished in an inert atmosphere such as nitrogen or under reduced pressure.

Prior to reduction, the catalyst composition may be optionally calcined. Preferably, the impregnated support is calcined at a temperature ranging from about 200 to about 700° C., more preferably from about 300 to about 500° C., for one minute or less, to about 3 hours or more. It is preferred, but not essential, that calcining be carried out in air. The drying step referred to above may be replaced by calcining or by reducing as described below.

The catalyst composition may then be reduced by contacting the composition with hydrogen at a temperature of from about 200° C. to about 700° C., preferably from about 300 to about 500° C., for about 30 minutes to about 24 hours or more. The reduced catalyst composition is best handled in the absence of air in order to maintain optimal performance and prevent pyrophoric behavior. The catalyst composition may be stabilized by gentle oxidation, carbon dioxide treatment, or other conventional techniques for stabilizing pyrophoric catalyst compositions, and may then be safely handled in air prior to its utilization. Before it is used, the stabilized catalyst composition is activated in hydrogen, typically at a temperature between about 150–250° C. Catalyst reduction or the activation of a reduced and stabilized catalyst composition may be accomplished in a separate step or in situ. The specific conditions for reduction are dependent on the particular catalyst composition being activated, as is known in the art, and on the desired activity and selectivity of the catalyst.

The amount of catalyst composition used in the reductive amination process of the invention depends on many variables including the relative proportions of the reactants, the reaction conditions, and the degree of conversion and selectivity desired. Moreover, the amount of catalyst composition will depend also on the nature of the catalyst composition itself, e.g., its metal loading, support composition and surface area, and the activity and age of the catalyst composition. The catalyst composition must be present in the reaction zone in sufficient catalytic amount to enable the desired reaction to occur.

The selectivity of the catalyst composition may be enhanced by the use of promoters. As used herein, a promoter is defined as any metal (or oxide) which when incorporated into the catalyst composition gives enhanced productivity and/or a higher selectivity to the preferred linear, low molecular weight products. In addition to boron, preferred metals or oxides for use as promoters are compounds containing elements selected from Group IA, Group IIA, Group IIIA, Group IVA, Group VA, Group VIA, Group VIIA, Group VIIIA, Group IB, Group IIB and Group IVB of the Periodic Table (IUPAC format). The preferred metals include, for example, copper, cobalt, chromium, rhodium, iridium, ruthenium, zinc, palladium, platinum, sodium, calcium, magnesium, strontium, lithium, potassium, barium, cesium, lanthanum, tungsten, iron, silver, titanium, manganese, niobium, aluminum, tin and mixtures of these metals. Especially preferred metals are magnesium, zinc, niobium, chromium, ruthenium, cobalt, copper, tin and mixtures thereof.

Promoters may be added to the catalyst composition either by co-impregnation with nickel and rhenium or they may be added to the support either before or after incorporation of the nickel and rhenium salts. It should also be understood that the nickel and rhenium need not be added simultaneously with each other or with the promoter; the promoter, nickel and rhenium combination may be added in any sequence. Promoters are added to the catalyst composition at preferred levels which are generally no higher than the nickel present in the catalyst composition on a weight percent basis. On a weight percent basis, a promoter/nickel ratio of 0 to about 0.5 is preferred.

The lower aliphatic alkane derivatives that may be aminated in accordance with the present invention are those that are well-known to those skilled in the art. These derivatives include those having one or more functional groups such as hydroxy, amino, imino, and carbonyl groups and combinations. Preferred lower aliphatic alkane derivatives include those containing one to six carbons. The functional groups present may be on the primary, secondary or tertiary carbon atoms. Examples of preferred lower aliphatic alkane derivatives include ethanol, ethylene glycol, monoethanolamine, dimethylethanolamine, diethylethanolamine, methylethanolamine, ethylenediamine, diethylenetriamine and higher polyamines, ethyleneimine, propanols, propanolamines, propanediols, acetone, butanols, butanediols, aminobutanols, pentanols, pentanediols, aminopentanols, hexanols, hexanediols, aminohexanols, hydroxyhexanals, hydroxycaproic acids, acetaldehyde, glyoxal, and glycolaldehyde. The lower aliphatic alkane derivatives also include compounds from which the aforementioned may be derived. Preferably, at least one of the functional groups in the lower aliphatic alkane derivative is a hydroxy group or amino group.

The particular lower aliphatic alkane derivative to be used depends, of course, upon the particular polyamine product or products desired. Often, the desired polyamine product differs from the lower aliphatic alkane derivative by the addition of an amino group, which replaces a non-amino functional group or adds a further amino group to a lower aliphatic alkane derivative. For example, ethylene glycol or monoethanolamine may be used as one of the lower aliphatic alkane derivatives in the production of ethylenediamine.

In one particularly useful amination process as taught by the invention, ethylenediamine is reacted with itself to produce diethylenetriamine. In this case, the lower aliphatic alkane derivative is ethylenediamine, which is reacted with an amine, also ethylenediamine. It has been discovered that the present catalyst composition has an especially high selectivity to diethylenetriamine in the reductive amination of ethylenediamine.

The amination process may be run using an excess of ammonia or amine to suppress reactions giving polyamine products. The ammonia or amine employed in the reaction may be anhydrous or may contain small amounts of water. With some catalytic systems a large excess of ammonia or amine must be present. In the present process, the ammonia or amine should be present in an amount at least equivalent to the stoichiometric amount required by the lower aliphatic alkane derivative. The ammonia or amine should preferably be present in an amount between 2 and 30 times the stoichiometric amount required. For example, in the production of ethylenediamine from ethylene glycol, monoethanolamine, or mixtures thereof, ammonia is preferably present in an amount such that the mole ratio of ammonia to ethylene glycol and/or monoethanolamine is in the range 4:1 to 25:1. Higher ratios are typically commercially unattractive.

Equipment and reaction conditions for reductive amination are well known in the art, and any such equipment and reaction conditions may be used. Generally, reaction temperatures within the range of about 125° to 350° C. are suitable, while a preferred range is 130° to 225° C. A relatively high pressure for the reaction is also preferred. Normally, the increased pressure is obtained by the amount of ammonia or amine and hydrogen already present in the reaction vessel, which is then heated to the reaction temperature. The reaction pressure should normally be about 400 to about 5,000 psig, preferably from 500 to about 3000 psig.

Hydrogen gas is generally present during the reductive amination reaction. Usually, the addition of hydrogen in an amount sufficient to bring the reaction mixture to the desired reaction pressure is sufficient.

Where selectivity is of primary concern in the amination process, it is preferred not to run the process to a high conversion. It has been found that selectivity to the preferred, linear polyamine products decreases as conversion increases. This is because higher molecular weight, more substituted polyamine products are produced as a result of a chain of consecutive reactions. That is, lower molecular weight polyamine products react among themselves to form higher molecular weight polyamine products and/or cyclize. However, where the catalyst composition is sufficiently selective for a particular polyamine product, it is possible to increase the rate of conversion while still maintaining a commercially acceptable level of selectivity. The ability to provide both high conversion rates and acceptable selectivity is an important economic advantage provided by the catalysts taught by the present invention.

The amination process of the present invention may be carried out in any conventional high pressure equipment having mixing and heating means. The process may be carried out in continuous or batch mode. The reactor design is also not narrowly critical and may consist of a stirred-tank, fixed-bed, slurry, fluid-bed or other designs well known in the art, using liquid-phase, gas-phase, multi-phase or super-critical conditions. The feed thereto may be upflowing or downflowing, and design features in the reactor that optimize plug flow may be employed.

The process is not limited to a confining set of conditions. The feed stream may be liquid, supercritical fluid, or gaseous, and the product stream taken from the reaction zone may be liquid, supercritical fluid, or gaseous. It is not necessary that the feed stream and the product stream be in the same physical state.

The reactants may be fed as a stream, typically continuously, to the reaction zone, a bed of the catalyst composition. The catalyst composition is usually in the form of solid particles (pellets, tablets, extrudates, spheres, etc.). Effluent from the reaction zone is also a stream comprising the unreacted components of the feed stream and the reaction products.

Reductive amination using the present catalyst composition advantageously provides polyamine product mixes containing higher amounts of low molecular weight, linear polyamines as compared to catalysts of the prior art at similar MEA conversions. More specifically, use of the catalyst composition provides an increased weight ratio of low molecular weight, linear polyamines to higher molecular weight and/or cyclic polyamines in the product stream. The catalyst composition is therefore highly advantageous for converting monoethanolamine into EDA at high selectivities with relatively less PIP and higher polyamines in the product mix. The catalyst composition is also highly effective for the reductive amination of ethylenediamine to diethylenetriamine, again with relatively lower amounts of PIP and higher polyamines formed.

The following examples further illustrate the invention. However, before turning to the examples in detail, it should be understood that the examples are included for illustrative purposes only and that the scope of the invention is in no way limited to the use of the particular Ni/Re and Ni/Re/B catalyst compositions set forth in the examples or to the use of MEA and ethylene glycol as the lower aliphatic alkane derivative being aminated. Similar results can be achieved using other catalyst compositions and derivatives consistent with the scope of the invention as disclosed herein.

Unless otherwise noted, all catalyst compositions were prepared using the following generalized procedure. Precursor salts of the nickel, rhenium and optionally boron were dissolved in 70–80° C. water to form an impregnation solution. The final volume of the impregnation solution was adjusted to equal three times the adsorption volume of the support to be impregnated, and the quantities of the precursor salts were those calculated to give the metal compositions provided in the Examples. In each case, the support was impregnated to incipient wetness by the addition of one-third of the hot impregnation solution and gently agitated until all the liquid had been adsorbed. The sample was then placed in a muffle furnace and calcined in air for one hour at 340° C., or as otherwise specified in the Examples. When the support had cooled, the impregnation and calcination steps were repeated two additional times. The impregnation solution was maintained at 70–80° C. throughout, and the final calcination time was increased from one to three hours. Those skilled in the art will appreciate that impregnation with the impregnation solution may optionally be done in one, two, four or more incipient wetness applications, as dictated by the solubility of the precursor salts, the porosity of the support to be impregnated, and the required weight loading of the metal.

Prior to use, the catalyst compositions were reduced in hydrogen by ramping the temperature at 3° C./min to 230° C., holding at this temperature for one hour, and then ramping at 3° C./min to 340° C., and holding for 3 hours, or as otherwise specified in the Examples. The catalyst compositions were allowed to cool under hydrogen to near room temperature. They were then stabilized by subjecting to a flowing stream of 10% air in nitrogen until the exotherm ceased. At no time was the exotherm allowed to exceed about 60° C.

The catalyst compositions were tested as powders using a microreactor system for the reductive amination of ethylene glycol, or as intact pellets in a small tubular reactor for the reductive amination of monoethanolamine (MEA) as described below.

Micro-reactor

A micro-reactor consisting of a 316-stainless steel tube that was 0.57 cm in diameter and 23 cm in length was used for the reductive amination of ethylene glycol with ammonia. Typically, 1–2 grams of 60/100 mesh catalyst (0.15–0.25 mm) was sandwiched between plugs of glass wool in the reactor tubes.

Prior to use, the catalyst compositions were treated (i.e., reduced or activated) in a reconfigured gas chromatograph unit. Catalyst compositions used immediately after calcination were reduced, while those that were reduced and stabilized were activated before use.

During catalyst reduction, the unit was ramped up in hydrogen flowing at 1.5 slph from 30° C. to 250–375° C. at 10° C./min and held at the final temperature for 3 hours. When reduction was complete, the catalyst compositions were purged with nitrogen flowing at 1.5 slph for 15 minutes and then cooled to ambient temperature. When reduced and stabilized catalysts were used they were first activated by heating at 180–200° C. for 15–24 hours under one atmosphere of flowing hydrogen. All gas flow rates were determined by calibrated rotameters. At ambient temperature, the micro-reactor was sealed without exposure to air and then inserted into a main reactor system.

Once the micro-reactor tubes were inserted into a temperature controlled oven, the reactor system was brought to reaction temperature and pressure with 3 slph of hydrogen flowing through the system. Ammonia and ethylene glycol were sequentially introduced into the hydrogen stream. Both the ammonia and hydrogen flow rates were regulated by mass-flow controllers. The flow rates of ammonia and ethylene glycol were adjusted so that the ammonia to glycol feed ratio was about 10:1. The ethylene glycol was pumped into the system so that space velocities ranging from 0.097 to 0.152 gmole/g catalyst/hr were obtained during reaction.

The reaction mixture was preheated before passing through the catalyst bed in a downflow mode. The back pressure on the system was controlled with back pressure regulators. The reactor effluent from the unit was decreased to normal pressures and the ammonia and hydrogen flashed in a tank, and then was passed through a scrubber. Liquid product was then collected and subsequently analyzed by capillary gas chromatography.

Tubular Reactor

A tubular reactor consisting of a 316-stainless steel tube having an inside diameter of 1.75 cm and an overall length of about 76 cm was used for the reductive amination of MEA with ammonia. Typically, 50 g of catalyst composition were packed into the central portion of the tube using 60 mesh (about 0.25 mm) glass beads to fill the void spaces between the catalyst pellets. Glass wool plugs held the catalyst bed in place.

In each case, the reduced and stabilized catalyst composition was activated by passing approximately 45 slph of hydrogen through the bed for 18 hours at 180° C. and atmospheric pressure. The reactor system was then brought to the temperature and pressure denoted in each specific example while still under hydrogen. A motor valve at the outlet of the reactor was used to control the system pressure.

When at the designated conditions, a solution of anhydrous ammonia and MEA (10:1 to 12:1 $NH_3$/MEA molar ratio) was pumped into the reactor at a MEA space velocity of about 10–12 gmole/kg cat/hr. Just prior to a preheater, hydrogen was introduced to the ammonia/MEA feed stream at a flow rate of about 15 slph. After passing through the preheater, which was maintained at reactor temperature, the mixture was passed into the reactor and over the catalyst bed composition via downward flow. Downstream of the pressure-control valve, the reaction mixture was passed into a receiver where the product was collected in a semi-batch fashion. The liquid product was condensed in the receiver at ambient temperature, allowing the ammonia and hydrogen to flash off. The condensed sample, which contained some unreacted ammonia, unreacted MEA and the products of reaction, was then analyzed for water by a Karl-Fisher procedure and for organic amines by capillary gas chromatography.

Each catalyst composition was typically tested at three to seven different temperatures, over the range of 145 to 175° C., to determine the effects of conversion on selectivity. The conversion and selectivity data thus obtained were subjected to curve fitting, and the resultant equation used to calculate selectivities at 30% MEA conversion. These 30% conversion values are used in Examples 1–6 for purposes of catalyst selectivity comparisons. Catalyst activities were compared by comparing MEA conversions obtained at a catalyst temperature of 160° C. Pressure and the MEA, $NH_3$ and hydrogen feed rates were held constant throughout.

EXAMPLE 1

In each of Examples 1A–1O, catalyst compositions containing 6.8 wt. % Ni, 1.8 wt. % Re, and 1.4 wt. % B on alumina-silica supports were used for the reductive amination of MEA with ammonia. The catalysts had varying support compositions and surface areas, and all supports were in the form of ⅛" extrudates, with the exception of that used in Example 1C, which was in the form of ⅜" pellets. The catalyst compositions were tested in the tubular reactor by the above described method, with the exception of Examples 1A through 1C, Example 1J, and Examples 1L through 1O, which had no glass beads admixed with the catalyst compositions. The results, shown in Table 1, demonstrate that catalyst compositions according to the present invention provide both high activities and high EDA selectivities.

EXAMPLE 2

In each of Examples 2A–2G, catalyst compositions containing 6.8 wt. % Ni and 1.8 wt, % Re on alumina-silica supports were prepared without the addition of boron. The catalysts had varying support compositions and support surface areas and were used for the reductive amination of MEA with ammonia as in Example 1, with the exception of Example 2B which had no glass beads admixed with the catalyst composition. All supports were in the form of ⅛" extrudates, and all catalyst compositions were tested by the above described method. The results, shown in Table 2, demonstrate that even in the absence of a boron promoter high activities and high EDA selectivities can still be obtained. Alumina-silica supports having higher surface areas are seen to be particularly effective.

EXAMPLE 3

In each of Examples 3A–3J, catalyst compositions were prepared on ⅛" extrudates of 80:20 alumina-silica having varied surface areas and pore volumes. The catalyst compositions were used for the reductive amination of MEA with ammonia as in Example 1. The nickel, rhenium and boron contents, and the catalyst composition preparation conditions were also varied; however, as shown in Table 3, the Re:Ni ratio was maintained at about 0.26. The results, shown in Table 3, taken together with the data contained in Tables 1 and 2, demonstrate that catalyst selectivity can be controlled to a high degree by appropriately selecting certain catalyst composition and preparation variables. More specifically, one can achieve very high EDA selectivities or, if desired, enhance the production of one or more of the co-products by these variations. The latter feature is demonstrated by the wide range of EDA/AEEA and EDA/PIP ratios that can be obtained.

Examples 3A and 3B demonstrate the effect that Ni loading can have on activity and selectivity. For these particular catalyst compositions increasing the Ni loading results in higher catalyst activity. However, increasing the Ni loading has a negative impact on the composition's selectivity for EDA, resulting in a less favorable EDA/PIP ratio. The data presented in Table 3 demonstrate that where high selectivity for EDA is important, the Ni loading must be appropriately selected along with other catalyst variables to ensure that the catalyst composition not only has acceptable activity, but also provides the desired mix of end products.

The effect of adding boron to the catalyst composition is illustrated in Examples 3C and 3D of Table 3. As illustrated, for these compositions increasing the boron concentration in the composition results in an increase in the catalyst composition's selectivity for EDA and a more favorable EDA/PIP ratio. Boron is seen to significantly decrease activity, however. This and the other drawbacks of high boron loadings and the need to keep boron loadings as low as practicable have been discussed above. The data in Table 3 show that where the boron content is reduced well below that shown in Example D, high selectivities for EDA and favorable EDA/PIP ratios can still be obtained by adjusting other catalyst parameters such as the Ni and Re loadings and the support surface area. The data in Table 2 demonstrate that this is the case even where the catalyst composition contains no boron.

Examples 3E and 3F and Examples 3G and 3H of Table 3 show, respectively, the effects of calcination temperature and reduction temperature on EDA selectivity. In both cases, as the temperature increases, the EDA selectivity decreases, accompanied by a corresponding decrease in EDA/PIP ratios. Examples 3E–3H show that these variables can have a significant impact on both selectivity and activity and must therefore be appropriately selected along with other catalyst variables depending on the particular level of activity and product mix desired.

The effect of support surface area on selectivity is shown in Examples 3I and 3J of Table 3. As shown in these examples, for these particular compositions increasing the surface area of the support results in a less active catalyst; however, higher selectivities for EDA and substantially more favorable EDA/PIP ratios are obtained. The other data presented in Table 3, as well as the data shown in Tables 1 and 2, demonstrate that by appropriately selecting support surface area together with other catalyst variables, catalyst compositions can be obtained that provide both high activity and enhanced selectivity for EDA.

EXAMPLE 4

Examples 4A–4P set forth in Table 4 further demonstrate the product mix flexibility which can be achieved by varying the appropriate catalyst composition and preparation variables as taught by the invention. As discussed above, it is presently commercially important to maximize both EDA selectivity and the EDA/PIP ratio. Examples 4A and 4J show different combinations of catalyst variables selected to provide high EDA selectivities. These examples should be viewed in connection with Example D in Table 3, since this particular example gave the highest EDA/PIP ratio of all of the catalyst compositions tested.

However, as also mentioned above, demands in the marketplace are constantly changing, and requirements for the product mix could also change substantially in the future. Accordingly, the appropriate catalyst variables in Example 4K were adjusted to provide enhanced selectivity for PIP and DETA, while the appropriate variables in Example 4L were adjusted to provide enhanced PIP, DETA and AEEA selectivity. In Examples 4M–4P, the catalyst variable were selected to provide enhanced DETA and AEEA selectivity.

Comparative Example 5

Catalyst compositions 5A–5I each contained 6.8 wt. % Ni, 1.8 wt. % Re and 1.4 wt. % B and were prepared on comparative alumina, silica and silica-alumina supports. These catalyst compositions were used for the reductive amination of MEA with ammonia as in Example 1, except no glass beads were used. The supports used in Examples 5A and 5B were in the form of 5 mm spheres, those used for Examples 5C, 5D, and 5F were in the form of 3/16" pellets, and the remainder were all ⅛" extrudates. The results are shown in Table 5.

The activities and EDA selectivities are inferior to those of the instant invention, i.e., catalyst compositions including silica-alumina supports with a silica content selected to vary from about 5 to about 65 weight percent. Example 5F further shows that the omission of boron from the catalyst composition on an alumina support leads to very inferior EDA selectivities. With respect to Examples 5E, 5H and 5I, it should be understood that while these catalyst compositions initially showed favorable activity and selectivity to EDA, the latter decreased substantially over time. Decreased selectivity for EDA over time, with a corresponding increase in the selectivity for AEEA, is a common problem associated with catalyst compositions prepared on alumina or alumina-silica supports having a very low silica content.

Comparative Example 6

Catalyst compositions 6A–6D each contained 6.8 wt. % Ni, 1.8 wt. % Re and 1.4 wt. % B and were prepared on comparative supports. These catalyst compositions were used for the reductive amination of MEA with ammonia as in Example 1, except no glass beads were used. The supports of Examples 6A and 6C were in the form of 3/16" extrudates, that of Example 6B was in the form of 1/8" tablets, and that of Example 6D was in the form of 1/16" extrudates. The results are shown in Table 6, and demonstrate that activities and EDA selectivities are inferior to those obtained with compositions prepared with an alumina-silica support.

EXAMPLE 7

Catalyst compositions 7A–7D were tested in the microreactor as described above for the reductive amination of ethylene glycol with ammonia. The catalyst compositions were evaluated as crushed powders.

The results shown in Table 7 demonstrate that the catalysts taught by the invention are highly active in the reductive amination of ethylene glycol. It should be noted that the composition of Example 7A has not been formulated in accordance with the invention and is for comparative purposes only. Example 7C additionally shows that boron is not necessary to obtain high EDA selectivities and EDA/PIP ratios, provided that factors such as the reduction temperature and the silica content and the surface area of the support are appropriately selected. Example 7D shows the superiority of high metal loadings.

TABLE 1

| | | | | Conv. @ | Wt. % Selectivity at 30% MEA Conversion | | | | | |
|---|---|---|---|---|---|---|---|---|---|---|
| Ex. | % SiO2 | SA | PV | 160° C. (a) | EDA | PIP | DETA | AEEA | E/A | E/P |
| A | 5 | 126 | 0.82 | 26 | 74 | 3.8 | 9.4 | 10.2 | 7.2 | 19.5 |
| B | 10 | 128 | 0.86 | 28 | 77 | 3.1 | 8.2 | 9.8 | 7.9 | 24.8 |
| C | 19 | 328 | 1.1 | 21 | 71 | 4.5 | 6.0 | 15.1 | 4.7 | 15.9 |
| D | 20 | 67 | 0.58 | 42 | 77 | 2.6 | 8.8 | 9.6 | 8.1 | 29.8 |
| E | 20 | 78 | 0.54 | 38 | 77 | 1.7 | 8.4 | 12.0 | 6.4 | 45.0 |
| F | 20 | 91 | 0.73 | 39 | 80 | 1.6 | 7.2 | 9.4 | 8.5 | 50.1 |
| G | 20 | 113 | 0.68 | 36 | 79 | 1.6 | 7.2 | 10.8 | 7.3 | 49.4 |
| H | 20 | 119 | 0.75 | 42 | 78 | 1.8 | 8.3 | 11.0 | 7.1 | 43.3 |
| I | 20 | 132 | 0.79 | 46 | 80 | 1.7 | 7.5 | 10.6 | 7.5 | 46.8 |
| J | 20 | 140 | 0.76 | 34 | 78 | 1.9 | 7.1 | 11.5 | 6.8 | 41.1 |
| K | 20 | 148 | 0.82 | 37 | 79 | 1.8 | 7.2 | 10.9 | 7.2 | 43.8 |
| L | 20 | 155 | 0.97 | 35 | 76 | 2.7 | 7.6 | 11.8 | 6.4 | 28.2 |
| M | 20 | 251 | 0.96 | 30 | 75 | 2.9 | 7.5 | 13.2 | 5.7 | 26.0 |
| N | 20 | 375 | 0.82 | 25 | 71 | 3.8 | 7.8 | 14.8 | 4.8 | 18.7 |
| O | 50 | 96 | 0.79 | 38 | 77 | 2.8 | 8.9 | 9.7 | 7.9 | 27.5 |

Abbreviations:
SA = surface area of the support (m²/g);
PV = pore volume of the support (ml/g);
EDA = ethylenediamine;
PIP = piperazine;
DETA = diethylenetriamine;
AEEA = aminoethylethanolamine;
E/A = EDA/AEEA wt. ratio;
E/P = EDA/PIP wt. ratio.
(a) MEA conversion observed at a reactor temperature of 160° C.

TABLE 2

| | | | | Conv. @ | Wt. % Selectivity @ 30% MEA Conversion | | | | | |
|---|---|---|---|---|---|---|---|---|---|---|
| No. | % SiO2 | SA | PV | 160° C. (a) | EDA | PIP | DETA | AEEA | E/A | E/P |
| A | 20 | 73 | 0.58 | 56 | 68 | 0.7 | 13 | 16 | 4.1 | 96.7 |
| B | 20 | 78 | 0.54 | 55 | 72 | 2.5 | 10 | 13 | 5.7 | 28.8 |
| C | 20 | 113 | 0.68 | 53 | 75 | 1.5 | 9 | 13 | 5.8 | 49.4 |
| D | 20 | 155 | 0.97 | 53 | 73 | 1.4 | 9 | 15 | 5.0 | 50.7 |
| E | 20 | 251 | 0.96 | 30 | 74 | 2.7 | 7 | 15 | 5.1 | 27.4 |
| F | 20 | 375 | 0.82 | 31 | 74 | 3.3 | 7 | 14 | 5.3 | 22.4 |
| G | 50 | 96 | 0.79 | 59 | 68 | 1.7 | 12 | 17 | 4.0 | 39.8 |

Abbreviations:
SA = surface area of the support (m²/g);
PV = pore volume of the support (ml/g);
EDA = ethylenediamine;
PIP = piperazine;
DETA = diethylenetriamine;
AEEA = aminoethylethanolamine,
E/A = EDA/AEEA wt. ratio,
E/P = EDA/PIP wt ratio.
(a) MEA conversion observed at a reactor temperature of 160° C.

TABLE 3

| Ex. | wt % Ni | wt % Re | wt % B | Calc'n. Temp | Red'n. Temp | SA | Conv. at 160 C. (a) | Wt. % Selectivity @ 30% MEA Conversion ||||||
|---|---|---|---|---|---|---|---|---|---|---|---|---|---|
| | | | | | | | | EDA | PIP | DETA | AEEA | E/A | E/P |
| A | 4.0 | 1.1 | 0.7 | 400 | 375 | 101 | 25.2 | 76.8 | 1.9 | 6.5 | 12.6 | 6.1 | 40.0 |
| B | 9.1 | 2.4 | 0.7 | 400 | 375 | 101 | 50.5 | 71.7 | 2.0 | 9.7 | 14.9 | 4.8 | 36.0 |
| C | 6.5 | 1.7 | 0 | 400 | 375 | 101 | 63.6 | 72.1 | 1.9 | 9.6 | 14.9 | 4.8 | 38.6 |
| D | 6.5 | 1.7 | 1.9 | 400 | 375 | 101 | 37.7 | 79.2 | 1.4 | 7.0 | 10.9 | 7.3 | 57.0 |
| E | 6.5 | 1.7 | 0.7 | 300 | 375 | 101 | 50.5 | 77.5 | 1.5 | 8.1 | 12.2 | 6.3 | 52.7 |
| F | 6.5 | 1.7 | 0.7 | 570 | 375 | 101 | 35.7 | 76.1 | 2.4 | 7.6 | 11.6 | 6.6 | 31.6 |
| G | 6.5 | 1.7 | 0.7 | 400 | 300 | 101 | 41.0 | 77.2 | 1.9 | 7.9 | 11.3 | 6.8 | 41.7 |
| H | 6.5 | 1.7 | 0.7 | 400 | 500 | 101 | 43.7 | 75.6 | 1.9 | 9.4 | 11.5 | 6.6 | 40.2 |
| I | 6.8 | 1.8 | 1.4 | 340 | 340 | 67 | 43.1 | 77.4 | 2.6 | 8.8 | 9.6 | 8.1 | 29.8 |
| J | 6.8 | 1.8 | 1.4 | 340 | 340 | 130 | 39.7 | 79.3 | 1.7 | 6.9 | 10.8 | 7.3 | 48.1 |

Abbreviations:
Calc'n: T = catalyst calcination temperature, °C.;
Red'n T = catalyst reduction temperature, °C;
SA = surface area of the support ($m^2/g$);
EDA = ethylenediamine;
PIP = piperazine;
DETA = diethylenetriamine;
AEEA = aminoethylethanolamine,
E/A = EDA/AEEA wt. Ratio,
E/P = EDA/PIP wt ratio.
(a) MEA conversion observed at a reactor temperature of 160° C.

TABLE 4

| Ex. | wt % Ni | wt % Re | wt % B | wt % SiO2 | Calc'n. Temp | Red'n. Temp | SA | Conv. at 160 C. (a) | Wt. % Selectivity @ 30% MEA Conversion ||||||
|---|---|---|---|---|---|---|---|---|---|---|---|---|---|
| | | | | | | | | | EDA | PIP | DETA | AEEA | E/A | E/P |
| A | 5.0 | 1.3 | 1.4 | 20 | 300 | 300 | 67 | 29.3 | 80.0 | 1.6 | 6.8 | 10.1 | 7.9 | 50.0 |
| B | 5.0 | 1.3 | 1.4 | 20 | 500 | 300 | 67 | 19.6 | 78.8 | 2.0 | 7.1 | 10.1 | 7.8 | 39.8 |
| C | 6.5 | 1.7 | 0.7 | 20 | 400 | 375 | 150 | 44.2 | 78.5 | 1.7 | 7.3 | 11.2 | 7.0 | 46.2 |
| D | 6.8 | 1.8 | 1.4 | 20 | 340 | 340 | 91 | 39.1 | 80.1 | 1.6 | 7.2 | 9.4 | 8.5 | 49.4 |
| E | 6.8 | 1.8 | 1.4 | 20 | 340 | 340 | 132 | 34.2 | 80.0 | 1.9 | 7.1 | 9.7 | 8.2 | 42.3 |
| F | 6.8 | 1.8 | 1.4 | 20 | 340 | 340 | 148 | 36.9 | 78.8 | 1.8 | 7.2 | 10.9 | 7.2 | 42.8 |
| G | 8.0 | 2.1 | 1.7 | 20 | 340 | 340 | 107 | 46.1 | 77.2 | 1.8 | 8.4 | 11.2 | 6.9 | 41.7 |
| H | 8.3 | 2.2 | 1.7 | 20 | 340 | 340 | 119 | 42.3 | 78.3 | 1.7 | 8.2 | 10.0 | 7.8 | 44.8 |
| I | 8.7 | 2.3 | 1.8 | 20 | 340 | 340 | 159 | 34.3 | 78.5 | 1.7 | 7.4 | 11.1 | 7.1 | 46.4 |
| J | 8.9 | 2.3 | 1.8 | 20 | 340 | 340 | 132 | 45.3 | 79.6 | 2.1 | 8.1 | 9.3 | 8.5 | 38.7 |
| K | 6.5 | 1.7 | 0.7 | 20 | 400 | 375 | 41 | 38.0 | 67.6 | 4.0 | 11.8 | 13.1 | 5.2 | 16.9 |
| L | 5.2 | 1.4 | 0 | 20 | 475 | 315 | 67 | 45.8 | 67.2 | 3.0 | 10.7 | 16.7 | 4.0 | 22.8 |
| M | 5.1 | 1.3 | 1.4 | 20 | 300 | 450 | 67 | 43.8 | 69.6 | 2.5 | 10.9 | 14.5 | 4.8 | 28.1 |
| N | 6.8 | 1.8 | 0 | 5 | 340 | 340 | 126 | 53.3 | 68.8 | 1.4 | 10.9 | 16.8 | 4.1 | 49.1 |
| O | 6.8 | 1.8 | 0 | 50 | 340 | 340 | 96 | 58.6 | 67.6 | 1.7 | 11.5 | 17.1 | 4.0 | 40.7 |
| P | 8.0 | 2.1 | 0 | 20 | 300 | 450 | 67 | 55.2 | 65.1 | 2.8 | 11.4 | 17.9 | 3.6 | 23.3 |

Abbreviations:
Calc'n. T = catalyst calcination temperature; °C.
Red'n T = catalyst reduction temperature, °C.;
SA = surface area of the support ($m^2/g$);
EDA = ethylenediamine;
PIP = piperazine;
DETA = diethylenetriamine;
AEEA = aminoethylethanolamine,
E/A = EDA/AEEA wt. Ratio,
E/P = EDA/PIP wt ratio.
(a) MEA conversion observed at a reactor temperature of 160° C.;

TABLE 5

| Ex. | Support | Support Composition wt. % SiO2 | Support Composition wt. % Al2O3 | SA | PV | Conv. @ 160° C. (a) | Wt. % Selectivity at 30% MEA Conversion ||||||
|---|---|---|---|---|---|---|---|---|---|---|---|---|
| | | | | | | | EDA | PIP | DETA | AEEA | E/A | E/P |
| A | SiO2/Al2O3 | 95 | 3 | 150 | 0.62 | 20 | 69 | 6.6 | 9 | 11 | 6.2 | 10.3 |
| B | SiO2/Al2O3 | 75 | 14 | 250 | 0.54 | 20 | 68 | 8.2 | 9 | 10 | 6.9 | 8.2 |

TABLE 5-continued

| Ex. | Support | Support Composition wt. % SiO2 | wt. % Al2O3 | SA | PV | Conv. @ 160° C. (a) | Wt. % Selectivity at 30% MEA Conversion EDA | PIP | DETA | AEEA | E/A | E/P |
|---|---|---|---|---|---|---|---|---|---|---|---|---|
| C | SiO2 | 100 | 0 | 180 | 0.90 | 29 | 67 | 4.5 | 8 | 16 | 4.1 | 14.8 |
| D | SiO2/Al2O3 | 98 | 2 | 60 | 0.42 | 30 | 70 | 6.2 | 10 | 11 | 6.3 | 11.3 |
| E | Al2O3 | 0 | 100 | 88 | 0.72 | 32 | 73 | 4.8 | 9 | 11 | 6.9 | 15.1 |
| F | Al2O3 (b) | 0 | 100 | 88 | 0.72 | 39 | 59 | 3.2 | 12 | 21 | 2.8 | 18.4 |
| G | SiO2/Al2O3 | 86 | 14 | 415 | 0.87 | 16 | 68 | 6.7 | 8 | 14 | 4.8 | 10.1 |
| H | SiO2/Al2O3 | 1 | 99 | 109 | 0.86 | 29 | 73 | 3.0 | 9 | 13 | 5.5 | 24.4 |
| I | SiO2/Al2O3 | 1 | 99 | 284 | 0.97 | 27 | 73 | 2.5 | 8 | 15 | 5.0 | 28.8 |

Abbreviations:
SA = surface area of the support (m²/g);
PV = pore volume of the support (ml/g);
EDA = ethylenediamine;
PIP = piperazine;
DETA = diethylenetriamine;
AEEA = aminoethylethanolamine,
E/A = EDA/AEEA wt. Ratio,
E/P = EDA/PIP wt ratio.
(a) MEA conversion observed at a reactor temperature of 160° C.
(b) Catalyst contains no boron.

TABLE 6

| No. | Support | SA | PV | Conv. @ 160° C. (a) | Wt. % Selectivity at 30% MEA Conversion EDA | PIP | DETA | AEEA | E/A | E/P |
|---|---|---|---|---|---|---|---|---|---|---|
| A | TiO2 | 35 | 0.24 | 58 | 27 | 4.2 | 15 | 38 | 0.7 | 6.3 |
| B | TiO2 | 8 | NA | 30 | 53 | 6.2 | 12 | 21 | 2.5 | 8.5 |
| C | TiO2/Al2O3 (88:12) | 116 | NA | 13 | 52 | 4.8 | 8 | 30 | 1.7 | 10.8 |
| D | ZrO2/SiO2 (75:25) | 130 | 0.24 | 27 | 64 | 7.9 | 11 | 11 | 5.6 | 8.1 |

Abbreviations:
SA = surface area of the support (m²/g);
PV = pore volume of the support (ml/g);
EDA = ethylenediamine;
PIP = piperazine;
DETA = diethylenetriamine;
AEEA = aminoethylethanolamine,
E/A = EDA/AEEA wt. ratio,
E/P = EDA/PIP wt ratio.
(a) MEA conversion observed at a reactor temperature of 160° C.

TABLE 7

| Ex. | Metals Loading (wt. %) | Support (a) | SA (m2/g) | PV (g/cc) | Tred (C.) | Trxn (C.) | P (psig) | Conv. (%) | Products | Select @ 20% Conv. |
|---|---|---|---|---|---|---|---|---|---|---|
| A | 6.8 Ni/1.8 Re/1.4 B | Al2O3—SiO2 (2:98) | 60 | 0.42 | 250 | 215 | 1600 | 25.0 | MEA | 42.6 |
| | | | | | | | | | EDA | 34.6 |
| | | | | | | | | | PIP | 6.7 |
| | | | | | | | | | DETA | 8.2 |
| | | | | | | | | | AEEA | 3.9 |
| | | | | | | | | | Heavies | 4.1 |
| | | | | | | | | | E/P | 5.2 |
| B | 6.8 Ni/1.8 Re/1.4 B | M2O3-SiO2 (80:20) | 139 | 0.77 | 300 | 216 | 1650 | 32.0 | MEA | 35.8 |
| | | | | | | | | | EDA | 49.1 |
| | | | | | | | | | PIP | 7.8 |
| | | | | | | | | | DETA | 3.9 |
| | | | | | | | | | AEEA | 1.5 |
| | | | | | | | | | Heavies | 1.9 |
| | | | | | | | | | E/P | 6.3 |

TABLE 7-continued

| Ex. | Metals Loading (wt. %) | Support (a) | SA (m2/g) | PV (g/cc) | Tred (C.) | Trxn (C.) | P (psig) | Conv. (%) | Products | Select @ 20% Conv. |
|---|---|---|---|---|---|---|---|---|---|---|
| C | 6.8 Ni/ 1.8 Re | Al2O3— SiO2 (80:20) | 140 | 0.76 | 250 | 215 | 1775 | 25.0 | MEA | 34.1 |
|   |   |   |   |   |   |   |   |   | EDA | 40.4 |
|   |   |   |   |   |   |   |   |   | PIP | 8.0 |
|   |   |   |   |   |   |   |   |   | DETA | 7.7 |
|   |   |   |   |   |   |   |   |   | AEEA | 4.0 |
|   |   |   |   |   |   |   |   |   | Heavies | 5.8 |
|   |   |   |   |   |   |   |   |   | E/P | 5.1 |
| D | 27.2 Ni/ 7.2 Re | Al2O3- SiO2 (80:20) | 132 | 0.79 | 375 | 180 | 1800 | 21.4 | MEA | 39.1 |
|   |   |   |   |   |   |   |   |   | EDA | 55.3 |
|   |   |   |   |   |   |   |   |   | PIP | 2.2 |
|   |   |   |   |   |   |   |   |   | DETA | 1.5 |
|   |   |   |   |   |   |   |   |   | AEEA | 0.4 |
|   |   |   |   |   |   |   |   |   | Heavies | 1.5 |
|   |   |   |   |   |   |   |   |   | E/P | 25.2 |

(a) Ratio in parenthesis refers to alumina-silica ratio.
Tred refers to the reduction temperature;
Trxn refers to the reaction temperature;
P refers to the reactor pressure;
E/P refers to EDA/PIP weight ratio.

What is claimed is:

1. A nickel/rhenium catalyst composition for reductive amination of a lower aliphatic alkane derivative, said catalyst composition comprising from about 2 to about 75 weight percent nickel and having a nickel to rhenium weight percent ratio of from about 1:1 to about 200:1, said nickel and rhenium being supported on an alumina-silica support which contains from about 5 to about 65 weight percent silica and which has a BET surface area of from about 30 to about 450 $m^2/g$.

2. The catalyst composition of claim 1, wherein the alumina-silica support comprises from about 10 to about 50 weight percent of silica.

3. The catalyst composition of claim 1, wherein the support has a BET surface area of from about 35 to about 300 $m^2/g$.

4. The catalyst composition of claim 3, wherein the support has a BET surface area of from about 50 to about 200 $m^2/g$.

5. The catalyst composition of claim 1, wherein the nickel to rhenium weight percent ratio is from about 1:1 to about 100:1.

6. The catalyst composition of claim 5, wherein the nickel to rhenium weight percent ratio is from about 2:1 to about 50:1.

7. The catalyst composition of claim 1 further comprising boron, wherein the weight percent ratio of boron to nickel is less than or equal to 1.

8. The catalyst composition of claim 7, wherein the weight percent ratio of boron to nickel is less than or equal to 0.5.

9. The catalyst composition of claim 7, wherein the support has a BET surface area of from about 60 to about 150 $m^2/g$.

10. The catalyst composition of claim 1, wherein the lower aliphatic alkane derivative is ethylene glycol and wherein the composition comprises from about 10 to about 75 weight percent nickel.

11. The catalyst composition of claim 10, wherein the composition comprises from about 10 to about 50 weight percent nickel.

12. The catalyst composition of claim 1, wherein the lower aliphatic alkane derivative is monoethanolamine or ethylenediamine and wherein the composition comprises from about 2 to about 30 weight percent nickel.

13. The catalyst composition of claim 12, wherein the composition comprises from about 2 to about 15 weight percent nickel.

14. The catalyst composition of claim 1, wherein the composition is calcined at a temperature of from about 200 to about 700° C.

15. The catalyst composition of claim 1, wherein the composition is reduced at a temperature of from about 200 to about 700° C.

16. The catalyst composition of claim 1, wherein the composition further comprises a promoter to enhance the selectivity of the composition.

17. The catalyst composition of claim 16, wherein the promoter comprises at least one element selected from the group consisting of Group IA, Group IIA, Group IIIA, Group IVA, Group VA, Group VIA, Group VIIA, Group VIIIA, Group IB, Group IIB, and Group IVB of the Periodic Table.

* * * * *